(12) United States Patent
Farnan et al.

(10) Patent No.: US 9,801,987 B2
(45) Date of Patent: Oct. 31, 2017

(54) BIFURCATED OUTFLOW CANNULAE

(71) Applicant: CircuLite, Inc., Teaneck, NJ (US)

(72) Inventors: Robert C. Farnan, Fort Lauderdale, FL (US); John P. Budris, Cheshire, CT (US)

(73) Assignee: CircuLite, Inc., Teaneck, NJ (US)

( * ) Notice: Subject to any disclaimer, the term of this patent is extended or adjusted under 35 U.S.C. 154(b) by 8 days.

(21) Appl. No.: 14/596,665

(22) Filed: Jan. 14, 2015

(65) Prior Publication Data
US 2015/0133720 A1 May 14, 2015

Related U.S. Application Data

(62) Division of application No. 12/860,106, filed on Aug. 20, 2010, now abandoned.

(60) Provisional application No. 61/259,347, filed on Nov. 9, 2009.

(51) Int. Cl.
*A61M 1/10* (2006.01)
*A61M 1/12* (2006.01)

(52) U.S. Cl.
CPC ............ *A61M 1/1008* (2014.02); *A61M 1/10* (2013.01); *A61M 1/122* (2014.02)

(58) Field of Classification Search
CPC ...... A61M 1/12; A61M 1/122; A61M 1/1012; A61M 1/1008; A61M 1/3659; A61M 1/1005

USPC .......................................... 600/16
See application file for complete search history.

(56) References Cited

U.S. PATENT DOCUMENTS

| 6,217,546 B1* | 4/2001 | Hinchliffe | A61M 29/02 604/508 |
| 2008/0058925 A1* | 3/2008 | Cohen | A61F 2/06 623/3.26 |
| 2009/0326463 A1* | 12/2009 | Ross | A61B 17/3423 604/167.01 |

OTHER PUBLICATIONS

Canadian Intellectual Property Office, Office Action in CA Application No. 2,776,137, dated May 19, 2016.

* cited by examiner

*Primary Examiner* — Niketa Patel
*Assistant Examiner* — Minh Duc Pham
(74) *Attorney, Agent, or Firm* — Wood Herron & Evans LLP

(57) ABSTRACT

A bifurcated cannula for directing blood into the arterial system. The bifurcated cannula including an ingress channel and first and second egress channels. The first egress channel directs a first portion of the blood entering the bifurcated cannula into the arterial system in a first direction. The second egress channel directs a second portion of the blood entering the bifurcated cannula into the arterial system in a direction that opposes the first direction.

12 Claims, 6 Drawing Sheets

BIFURCATED OUTFLOW CANNULAE

CROSS-REFERENCE TO RELATED APPLICATION

This application is a divisional of U.S. patent application Ser. No. 12/860,106, filed Aug. 20, 2010 (pending) which claims the priority of U.S. Provisional Patent Application Ser. No. 61/259,347, filed on Nov. 9, 2009, the disclosures of which are incorporated by reference herein.

TECHNICAL FIELD

The present invention relates generally to devices for assisting the heart in moving blood through the body; more specifically the invention relates to pump outflow cannulae.

BACKGROUND

The circulatory system of the human body transports blood containing chemicals, such as metabolites, hormones, and cellular waste products, to and from the cells. This organ system includes the heart, blood, and a vascular network. Veins are vessels that carry blood toward the heart while arteries carry blood away from the heart. The human heart consists of two atrial chambers and two ventricular chambers. Atrial chambers receive blood from the veins and the ventricular chambers, which include larger muscular walls, pump blood from the heart. Movement of the blood is as follows: blood enters the right atrium from either the superior or inferior vena cava and moves into the right ventricle. From the right ventricle, blood is pumped to the lungs via pulmonary arteries to become oxygenated. Once the blood has been oxygenated, the blood returns to the heart by entering the left atrium, via the pulmonary veins, and flows into the left ventricle. Finally, the blood is pumped from the left ventricle into the aorta and the vascular network.

In some instances, it becomes necessary to maintain fluidic communication with the vascular network. For example, a circulatory assist system uses a pump to aid in moving blood through the vascular network, thereby relieving the symptoms associated with congestive heart failure (commonly referred to as heart disease). The pump of the circulatory assist system includes inflow and outflow cannulae. Often the inflow cannula connects the left side of the heart to the pump; the outflow cannula connects the pump to the arterial network.

However, the fluidic output of the pump will often greatly exceed the natural fluid capacity of the particular artery used for implanting the outflow cannula. The insufficiency of the venous network to then immediately compensate for the increased blood inflow may result in edema of the extremity immediate to the implanted outflow cannula. While the venous network may adapt and compensate over time, it would be beneficial to have devices that better distribute the fluid flow from the pump in a manner that would prevent the initial occurrence of swelling.

SUMMARY

In one illustrative embodiment, the present invention is directed to a bifurcated cannula for directing blood into the arterial system. The bifurcated cannula including an ingress channel and first and second egress channels. Blood from a pump flows into the bifurcated cannula through the ingress channel. The first egress channel directs a first portion of the blood entering the bifurcated cannula into the arterial system in a first direction. The second egress channel directs a second portion of the blood entering the bifurcated cannula into the arterial system in a direction that opposes the first direction.

DETAILED DESCRIPTION

Figure 1:
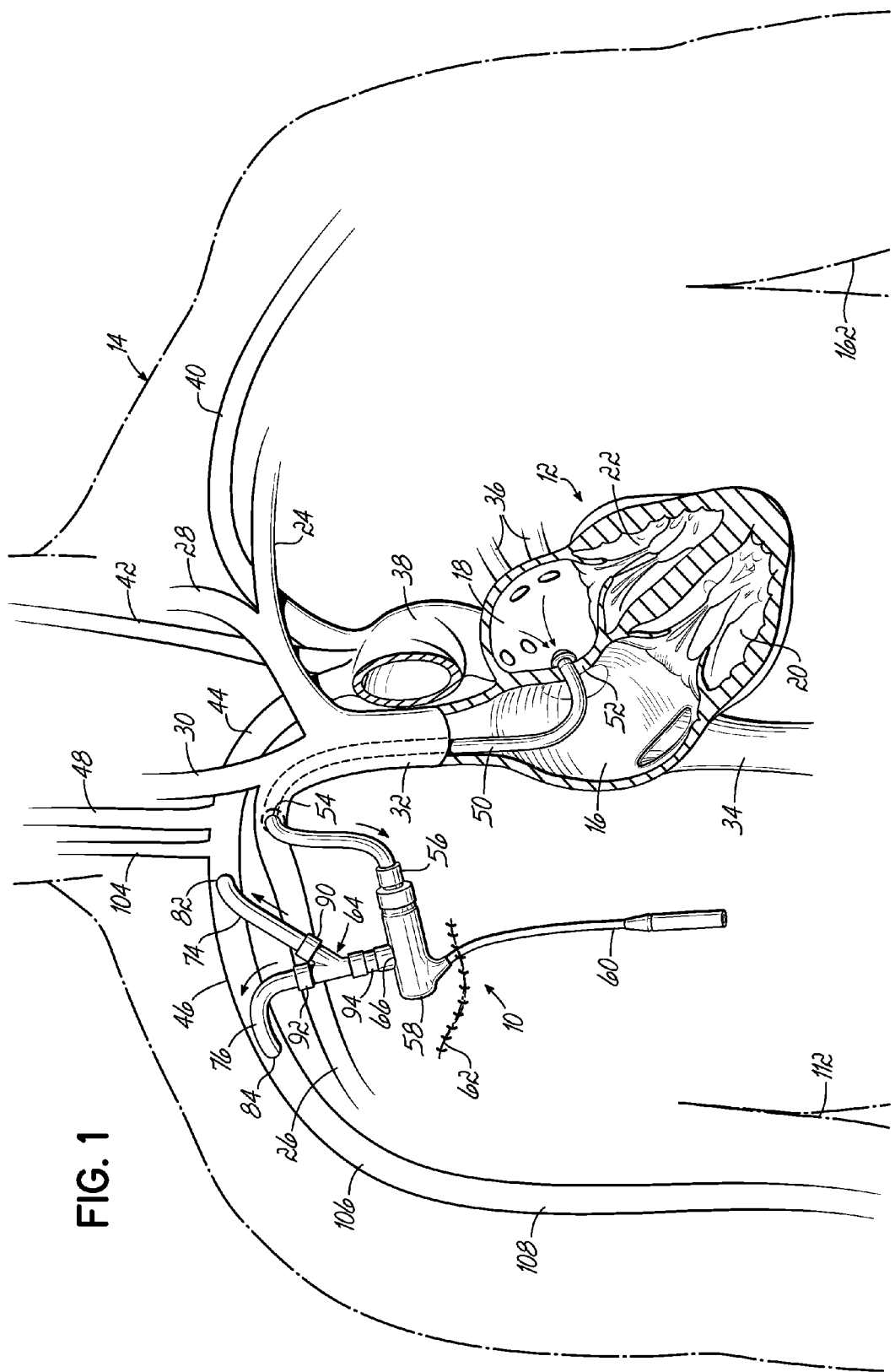
FIG. 1 is a diagrammatic view of a circulatory assist system with the outflow of the pump being connected to the right subclavian artery by a bifurcated cannula, with the heart shown in cross-section.

FIG. 1 illustrates an implanted circulatory assist system 10. For illustrative purposes, certain anatomy is shown including the heart 12 of a patient 14 having a right atrium 16, a left atrium 18, a right ventricle 20, and a left ventricle 22. Blood from the left and right subclavian veins 24, 26 and the left and right jugular veins 28, 30 enters the right atrium 16 through the superior vena cava 32 while blood from the lower parts of the body enters the right atrium 16 through the inferior vena cava 34. The blood is pumped from the right atrium 16, to the right ventricle 20, and to the lungs (not shown) to be oxygenated. Blood returning from the lungs enters the left atrium 18 via pulmonary veins 36 and is then pumped into the left ventricle 22. Blood leaving the left ventricle 22 enters the aorta 38 and flows into the left subclavian artery 40, the left common carotid 42, and the brachiocephalic trunk 44 including the right subclavian artery 46 and the right common carotid 48.

With respect to the implanted circulatory assist system 10, a flexible cannula body 50 extends from within the left atrium 18, through the intra-atrial septum 52, and percutaneously to a vascular access site 54 in the right subclavian vein 26. The flexible cannula body 50 is attached to an input port 56 of an implantable pump 58. Though not shown, the flexible cannula body 50 may alternatively be surgically implanted into the heart 12 and extend to the pump 58 through the thoracic cavity.

The pump 58 may be an axially-driven pump with an impeller (not shown). Those skilled in this art, however, recognize that other types of pumps may be used in other embodiments but may include pumps such as those described in U.S. application Ser. No. 11/627,444, published as 2007/0197854, which is incorporated herein by reference in its entirety. The suitable pump 58 for use with the circulatory assist system 10 may be capable of pumping blood.

A cable 60 can extend transdermally from the pump 58 to a position in the abdomen where the cable 60 exits the patient 14 and may connect to a power supply (not shown). Suitable power supplies may be any universal-type power supply that sends power to the pump 58 via the cable 60 and may include, but is not limited to, a rechargeable battery pack.

The physician may position the implantable pump 58 at least subcutaneously and, optionally, submuscularly in a pump pocket 62 located near the vascular access site 54, or alternatively, maintain the pump 58 externally.

A bifurcated outflow cannula 64 connects an output port 66 of the implantable pump 58 to a suitable artery, illustrate here as the right subclavian artery 46. One skilled in the art would understand that while the bifurcated outflow cannula 64 is illustrated as extending over the right subclavian vein 26 to the right subclavian artery, in practice the bifurcated outflow cannula 64 would likely reside beneath the right subclavian vein 26.

Figure 2:
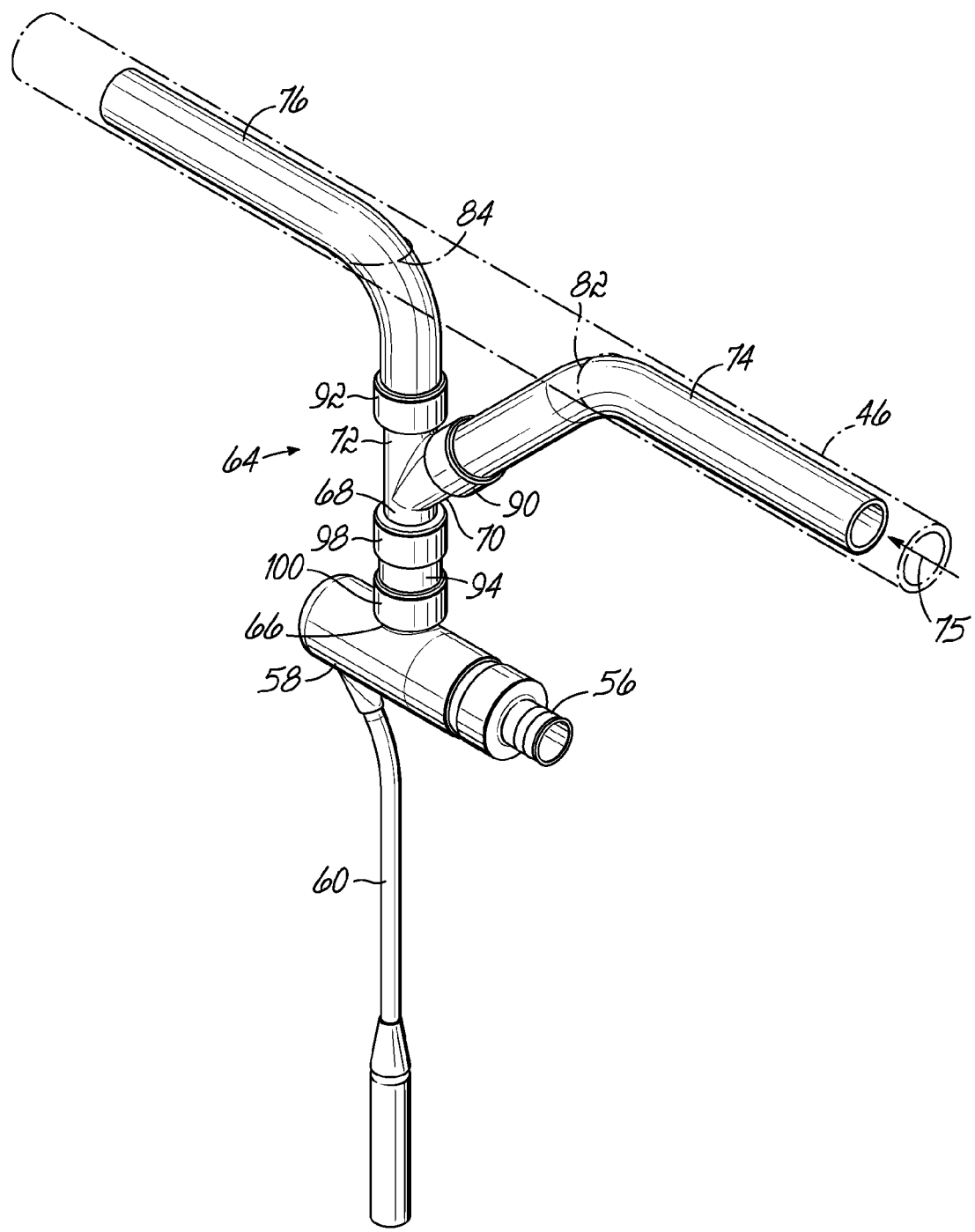
FIG. 2 is a perspective view of one exemplary embodiment of a bifurcated outflow cannula connected to the right subclavian artery and an implantable pump.
Figure 3:
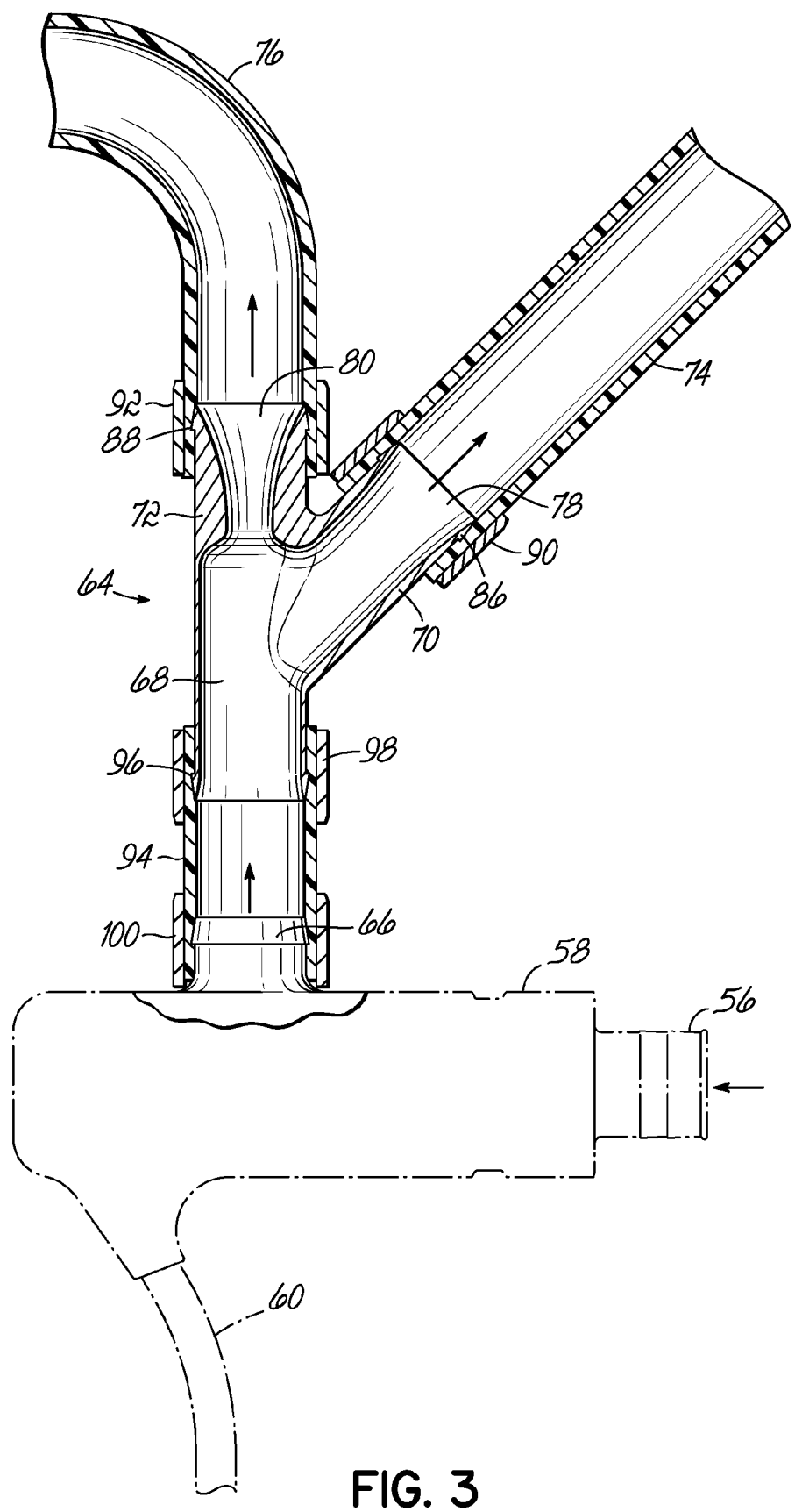
FIG. 3 is a cross-sectional view of the bifurcated outflow cannula shown in FIG. 2.

FIGS. 2 and 3 illustrate the bifurcated outflow cannula 64 formed as a y-connector having an ingress channel 68 and first and second egress channels 70, 72. The first egress channel 70, as illustrated, directs blood into the right subclavian artery 46 via a first stent graft 74 and in a direction that opposes (i.e., retrograde) the native blood flow direction of the right artery 46, illustrated by arrow 75. The second egress channel 72, as illustrated, directs blood into the artery 46 via a second stent graft 76 and in a direction that is the same (i.e., radial) as the native blood flow direction of the right subclavian artery 46. The stent grafts 74, 76 may be any commercially-available self expanding, covered, endovascular stent graft, such as the FLAIR, which is manufactured by Bard Peripheral Vascular (Tempe, Ariz.) or the covered WALLSTENT by Boston Scientific (Natick, Mass.). As illustrated, the size of the stent grafts 74, 76 are selected to allow for a minimum of about 5 cm engagement within the vascular structure and up to about 10 cm of length outside of the vascular structure for connection to the bifurcated outflow cannula 64; however, the size and lengths of the stent grafts 74, 76 should not be limited to those specifically shown.

FIG. 3 illustrates the further details of the bifurcated outflow cannula 64 in cross-section. The bifurcated outflow cannula 64 may be machined from a metallic material, for example titanium, and polished to minimize the incidence of thrombus formation; alternatively, the bifurcated outflow cannula 64 may be molded from a polymeric material, such as silicone or urethane.

The egress channels 70, 72 are constructed to permit a desired, relative amount of blood flow in the radial and retrograde directions. As shown, the second egress channel 72 branches distal to the first egress channel 70; however, other arrangements may be used. The egress channels 70, 72 are constructed with lumens 78, 80 having relative cross-sectional areas that are selected to provide a retrograde:radial flow ratio that is approximately 80:20 to meter the blood flow from the pump 58. Accordingly, a first flow through the first egress channel 70 in the retrograde direction will be high volume while a second flow through the second egress channel 72 in the radial direction will be low volume. Though not specifically shown, it is possible to construct the cross-sectional areas such that the ratios are 50:50 or other ratios as desired, but generally the volume directed in the retrograde direction will meet or exceed the volume directed in the radial direction.

Referring now to FIGS. 1, 2, and 3, in use, the physician creates first and second vascular incisions 82, 84 in the appropriate vascular structure, illustrated here as the right subclavian artery 46. The first and second stent grafts 74, 76 are directed into and deployed in the right subclavian artery 46 in a manner that is well known to one that is skilled in the art and that accommodates placement of the bifurcated outflow cannula 64.

The physician then positions the proximal ends of the stent grafts 74, 76 over an outer surface of the respective egress channels 70, 72 of the bifurcated outflow cannula 64. The outer surface may be constructed to include one or more barbs 86, 88 for providing resistance against the undesired removal of the stent grafts 74, 76. Graft collets 90, 92 may then be used to clamp and secure the stent grafts 74, 76 onto the egress channels 70, 72 in a manner that is known.

If desired, the physician may connect an extension tube 94 between the ingress channel 68 and the outflow port 66 of the pump 58. In this way, the pump 58 may be positioned at a desired distance from the right subclavian artery 46. The extension tube 94 may be constructed from a biodurable, low durometer thermoplastic or thermoset elastomer material. Coupling of the extension tube 94 to the ingress channel 68 may include directing a distal end of the extension tube 94 over the outer surface of the ingress channel 68, which may also include one or more barbs 96. The extension tube 94 may then be secured with a collet 98 and in a manner that is similar to the methods described above. Another collet 100 may be used to secure the extension tube 94 to the outflow port 66 of the pump 58.

With the fluidic coupling complete, the circulatory assist system 10 may be used to aid the heart 12 in pumping the patient's blood through the vascular network as was shown in FIG. 1. Accordingly, blood flow can proceed in the native manner with oxygenated blood traveling from the left atrium 18 into the left ventricle 22 to the aorta 38. From the aorta 38, blood moves into the left subclavian artery 40, the left common carotid 42, and the brachiocephalic trunk 44. Blood flow may also proceed along the artificial path by entering the flexible cannula body 50 from the left atrium 18 and traveling through the lumen of the flexible cannula body 50 to the pump 58.

From the pump 58, blood flows into the bifurcated outflow cannula 64, which is then distributed in a manner that is consistent with the selected retrograde:radial ratio. For example, with the illustrated bifurcated outflow cannula 64 having the retrograde:radial ratio of 80:20, the majority of the blood will be directed in the retrograde direction. Because the pump 58 is typically operated within a range of about 2 L/min to about 3 L/min and the native flow rate of the right subclavian artery 46 is about 0.5 L/min, the blood pumped in the retrograde direction will overpower the native flow into the right subclavian artery 46. Accordingly, the net blood flow in the right subclavian artery 46 that is distal to the first egress channel 70 will be in the retrograde direction into the brachiocephalic trunk 44, and even the aorta 38. From there, the blood is redistributed, for example, into other arteries, such as the carotid arteries 42, 48 and the vertebral artery 104. The other 20% of the blood flow is directed radially, in the native blood flow direction of the right subclavian artery 46 and, accordingly, will enter the axillary artery 106 and the brachial artery 108 of the right arm 112. In this way, blood is supplied to the patient's right arm 112 or the extremity downstream of the select artery while not overwhelming the venous capacity to remove the same and thus eliminating edema.

Figure 4:
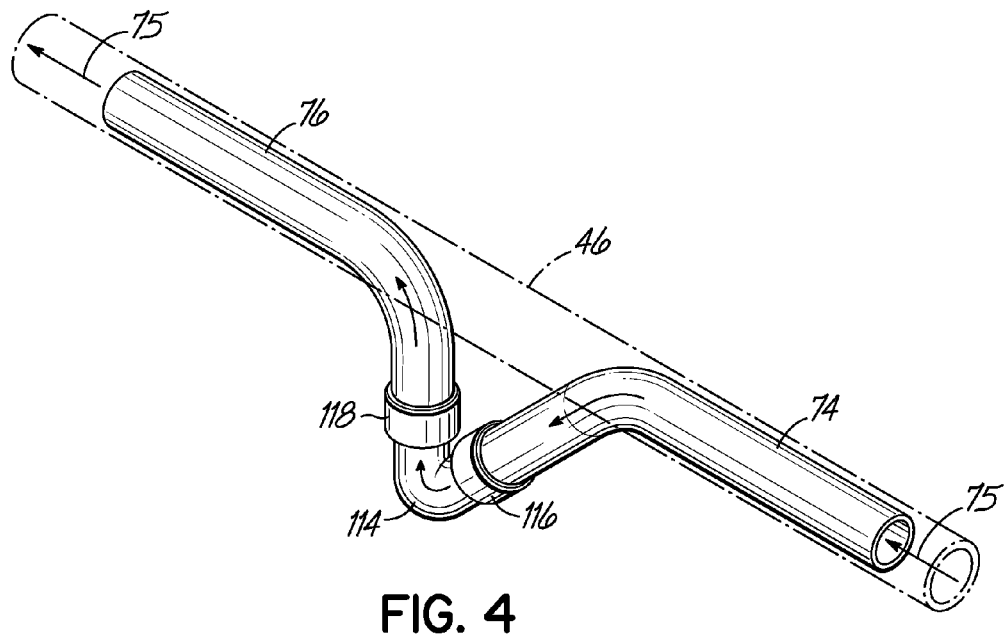
FIG. 4 is a perspective view of an exemplary method of removing the bifurcated outflow cannula and connecting the stent grafts.

In some patients, there may be a time after the surgery in which the circulatory assist system 10 is no longer necessary. Thus, it would be beneficial to remove the unnecessary components, such as the implantable pump 58 and the flexible cannula body 50. However, the decrease in blood flow in the portion of the right subclavian artery 46 between the stent grafts 74, 76 will have caused the vessel to thrombus completely and become occluded within a short time after the circulatory assist system 10 is implanted. One exemplary method of reversing the procedure and continuing blood flow through the right subclavian artery 46 is illustrated in FIG. 4.

As shown, once the pump 58 (FIG. 1) and flexible cannula body 50 (FIG. 1) have been removed, the extension tube 94 (FIG. 2) and bifurcated outflow cannula 64 (FIG. 2) are also removed. The stent grafts 74, 76 are then coupled together using a U-shaped adaptor 114. The U-shaped adaptor 114 may be constructed in a manner that is similar to the bifurcated outflow cannula 64 (FIG. 3), namely, machined from a metallic material and polished, or molded from a polymeric material. The adaptor 114 may include barbs (not shown) located near the ingress and egress openings, in a manner similar to the bifurcated outflow cannula 64 (FIG. 3), for attaching the first and second stent grafts 74, 76. Collets 116, 118 may then be used to secure the stent grafts 74, 76 to the adaptor 114.

With the circulatory assist system 10 (FIG. 1) removed, blood will flow only in accordance with the native path, which was described in detail above. Blood entering the right subclavian artery 46 will be unable to traverse the portion of the vessel residing between the stent grafts 74, 76. Instead, blood will flow through the stent grafts 74, 76 and the U-shaped adaptor 114 and then to the axillary artery 106 (FIG. 1).

While the manner of reversing the procedure has been shown with a U-shaped adaptor 114 and the right subclavian artery 46, it would be understood that adaptors having other shapes could also be used in other vascular structures.

Figures 5A, 5B:
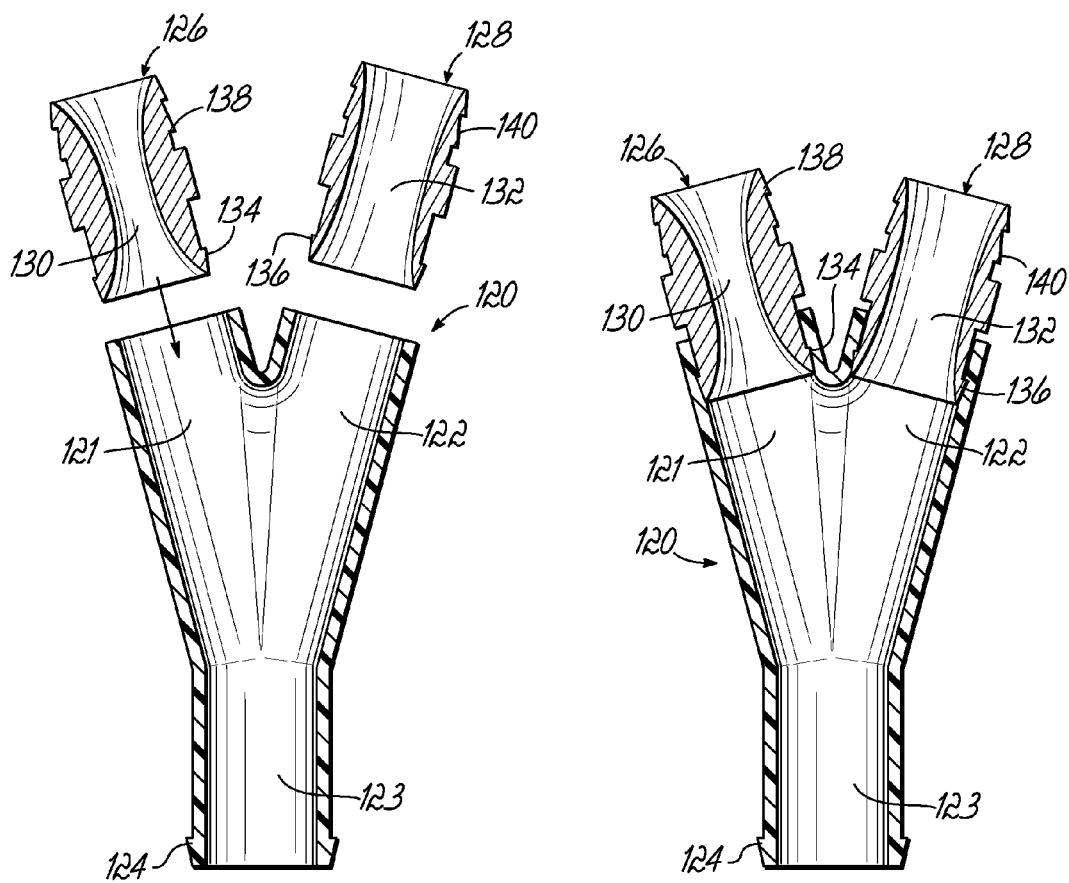
FIG. 5A is a cross-sectional view of another embodiment of a bifurcated outflow cannula with a channel fitting.
FIG. 5B is a view similar to FIG. 5A, but showing the channel fitting assembled with the bifurcated outflow cannula.

FIGS. 5A and 5B illustrate a bifurcated outflow cannula 120 having an alternate Y-shaped configuration where egress channels 121, 122 are constructed to diverge angularly from the same point distal to the ingress channel 123. Construction of the alternate bifurcated outflow cannula 120 may be in accordance with the methods described previously. The ingress channel 123 may include a barb 124 for receiving an extension tube 94 (FIG. 2); however, it would be understood that the ingress channel 123 could also couple directly to the output port 66 (FIG. 1) of the pump 58 (FIG. 1), with or without the use of a collet. To achieve a desired retrograde:radial flow ratio, channel fittings 126, 128 may be constructed and fitted into the egress channels 121, 122, respectively. Each channel fitting 126, 128 will include an internal lumen 130, 132 having an internal cross-sectional area for determining the retrograde:radial flow ratio. The channel fittings 126, 128 may include barbs 134, 136 for coupling to the respective egress channel 121, 122. Glue, epoxy, or welding may be used to secure the channel fittings 126, 128. Additional barbs 138, 140 may be included on the channel fittings 126, 128 for receiving the stent grafts 74, 76 (FIG. 1).

Figure 6:
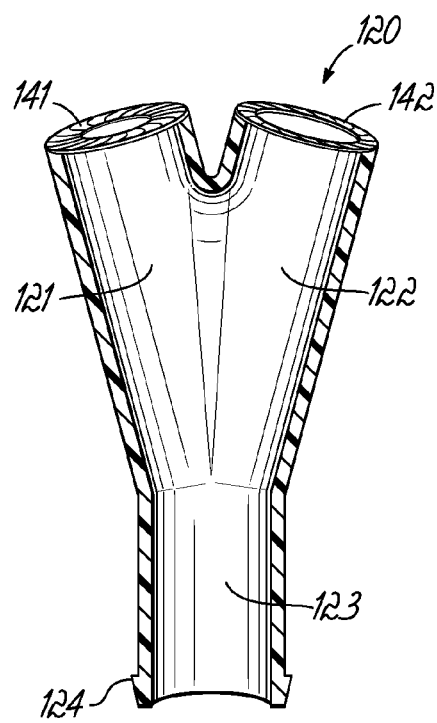
FIGS. 6-8 are cross-sectional views of additional embodiments of the bifurcated outflow cannulae.
Figure 7:
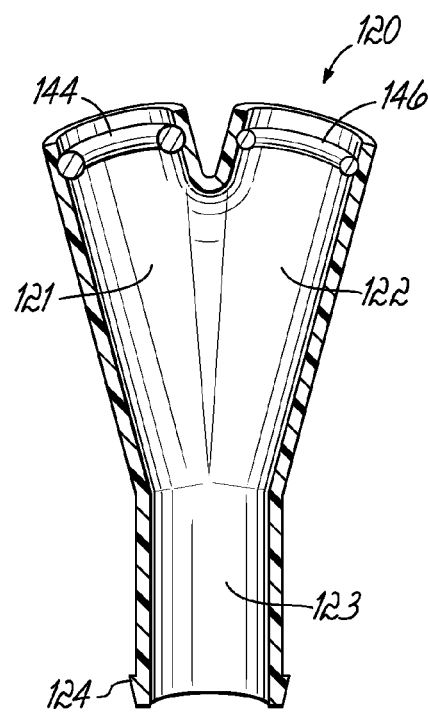

FIGS. 6 and 7 illustrate yet two additional manners of constructing the bifurcated outflow cannula 120 where the desired retrograde:radial ratio is selected by the inclusion of a flow selector. The flow selectors in FIG. 6 include irises 141, 142 having different inner diameters; the flow selectors in FIG. 7 include rings 144, 146 also having different inner diameters. While these figures specifically illustrate the flow selectors within the egress channels 121, 122, it would be understood that the flow selectors could be positioned alternatively, or additionally, in the ingress channel 123, a position between the ingress channel 123 and one of the egress channels 121, 122, or in a combination of these positions. Further, it would be understood that the flow selectors could be positioned in any one of the various embodiments of the bifurcated outflow cannula and can be mixed to suit a particular function.

Figure 8:
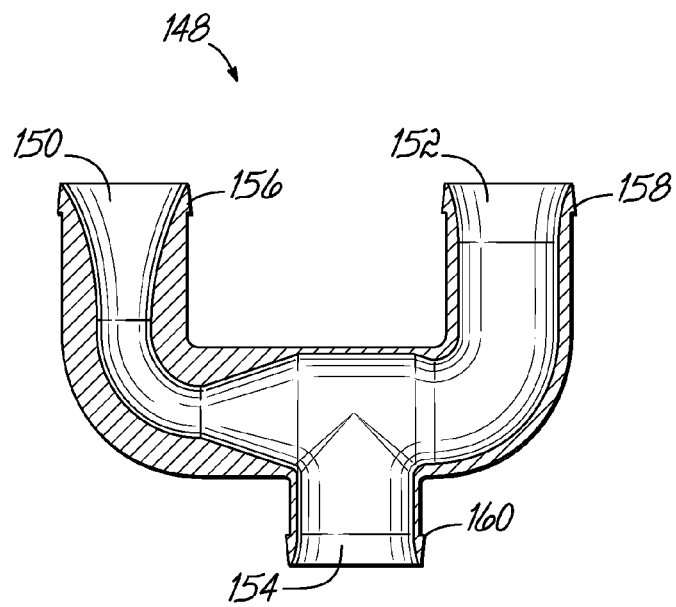

FIG. 8 illustrates yet another alternate configuration of the bifurcated outflow cannula 148, formed as a t-connector. In this particular configuration, the egress channels 150, 152 form a 90° angle with respect to the ingress channel 154 and form a 180° angle therebetween. While the illustrative embodiment is shown with an 80:20 ratio, which was molded or machined, it would be understood that the channel fittings 126, 128 of FIGS. 5A and 5B could alternatively be used. One or more of the channels 150, 152, 154 may be constructed with barbs 156, 158, 160 for securing the stent grafts 74, 76 (FIG. 2) as described previously.

Figure 9:
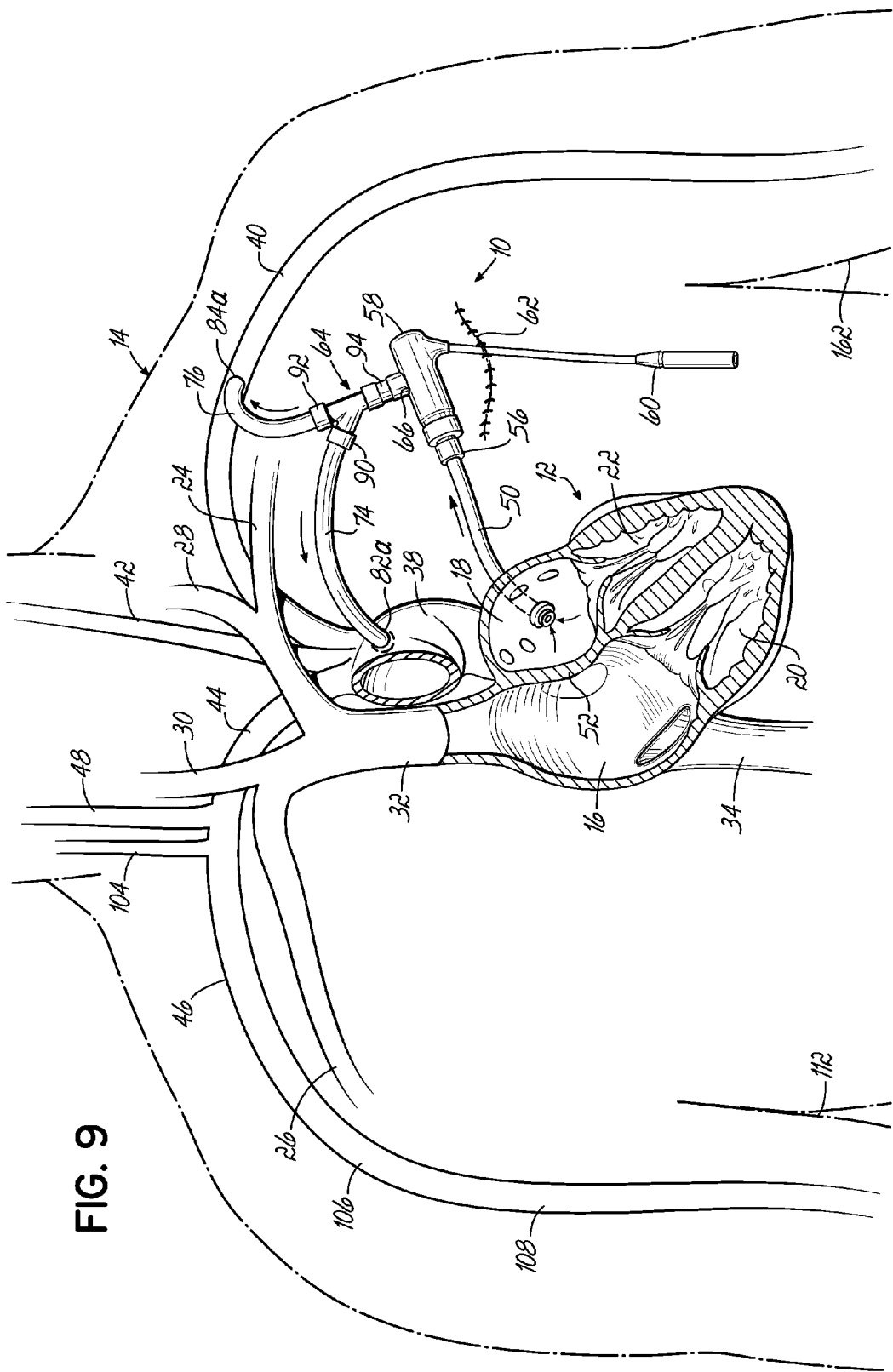
FIG. 9 is a diagrammatic view of an alternate method of implanting the circulatory assist system, with the heart shown in cross-section.

It would be appreciated by one skilled in the art that the egress channels need not necessarily direct blood into the same arterial vessel. FIG. 9 illustrates another method of using the bifurcated cannula 64 where the first stent graft 74 enters the aorta 38 at the first vascular incision 82a and the second stent graft 76 enters the left subclavian artery 40 at the second vascular incision 84a. In this way, the low volume blood flow is directed into the left subclavian artery 40 for the left arm 162 while the high volume blood flow is directed into the aorta 38 for distribution amongst the left subclavian artery 40, the left common carotid 42, and the brachiocephalic trunk 44. FIG. 9 also illustrates the flexible cannula body 50 being surgically positioned into the left atrium 18.

While only a few specific configurations are shown, it would be understood that various arrangements are possible having a single ingress channel and two egress channels.

While the present invention has been illustrated by a description of various preferred embodiments and while these embodiments have been described in some detail, it is not the intention of the Applicant to restrict or in any way limit the scope of the appended claims to such detail. Additional advantages and modifications will readily appear to those skilled in the art. The various features of the invention may be used alone or in any combination depending on the needs and preferences of the user. This has been a description of the present invention, along with the preferred methods of practicing the present invention as currently known. However, the invention itself should only be defined by the appended claims.

What is claimed is:

1. A method of directing blood from a pump to the arterial system using a bifurcated cannula comprising an ingress channel and first and second egress channels, and first and second stent grafts having proximal and distal ends, the method comprising:
   directing the blood from the pump into the ingress channel of the bifurcated cannula;
   directing a first portion of the blood entering the bifurcated cannula from the ingress channel through the first egress channel;
   directing a second portion of the blood entering the bifurcated cannula from the ingress channel through the second egress channel;
   inserting the distal end of the first stent graft into the arterial system;
   inserting the distal end of the second stent graft into the arterial system;
   expanding the first stent graft to fluidicly couple the distal end of the first stent graft to the arterial system;

expanding the second stent graft to fluidicly couple the distal end of the second stent graft to the arterial system;
fluidicly coupling the proximal end of the first stent graft to the first egress channel;
fluidicly coupling the proximal end of the second stent graft to the second egress channel;
directing the first portion of the blood from the first egress channel through the first stent graft into the arterial system;
directing the second portion of the blood from the second egress channel through the second stent graft into the arterial system;
disengaging the first and second egress channels from the respective proximal ends of the first and second stent grafts; and
fluidicly coupling the first and second stent grafts such that the blood flowing in a first direction enters the first or second stent graft and flows into the other of the first or second stent graft in the first direction and then flows back into the arterial system in the first direction.

2. The method according to claim 1, wherein directing the first portion of the blood from the first egress channel through the first stent graft into the arterial system; and directing the second portion of the blood from the second egress channel through the second stent graft into the arterial system comprises:
directing the first portion of the blood from the first egress channel through the first stent graft into the arterial system in a first direction; and
directing the second portion of the blood from the second egress channel through the second stent graft into the arterial system in a second direction that opposes the first direction.

3. The method according to claim 2, wherein directing the first portion of the blood from the first egress channel through the first stent graft into the arterial system in a first direction; and directing the second portion of the blood from the second egress channel through the second stent graft into the arterial system in a second direction that opposes the first direction comprises:
directing the first portion of the blood from the first egress channel through the first stent graft into the arterial system in a retrograde direction; and
directing the second portion of the blood from the second egress channel through the second stent graft into the arterial system in a radial direction.

4. The method according to claim 3, wherein directing the first portion of the blood from the first egress channel through the first stent graft into the arterial system in a retrograde direction; and directing the second portion of the blood from the second egress channel through the second stent graft into the arterial system in a radial direction comprises:
directing the first portion of the blood having a first volume from the first egress channel through the first stent graft into the arterial system in a retrograde direction; and
directing the second portion of the blood having a second volume from the second egress channel through the second stent graft into the arterial system in a radial direction,
wherein the first volume exceeds the second volume.

5. The method according to claim 1, further comprising:
securing the proximal end of the first stent graft over an outer surface of the first egress channel; and
securing the proximal end of the second stent graft over an outer surface of the second egress channel.

6. The method according to claim 1, further comprising:
directing the blood from the left atrium of a heart to the pump.

7. The method according to claim 1, wherein inserting the distal end of the first stent graft into the arterial system;
inserting the distal end of the second stent graft into the arterial system;
expanding the first stent graft to fluidicly couple the distal end of the first stent graft to the arterial system;
expanding the second stent graft to fluidicly couple the distal end of the second stent graft to the arterial system;
directing the first portion of the blood from the first egress channel through the first stent graft into the arterial system; and
directing the second portion of the blood from the second egress channel through the second stent graft into the arterial system comprises:
inserting the distal end of the first stent graft into the right subclavian artery;
inserting the distal end of the second stent graft into the right subclavian artery;
expanding the first stent graft to fluidicly couple the distal end of the first stent graft to the right subclavian artery;
expanding the second stent graft to fluidicly couple the distal end of the second stent graft to the right subclavian artery;
directing the first portion of the blood from the first egress channel through the first stent graft into the right subclavian artery; and
directing the second portion of the blood from the second egress channel through the second stent graft into the right subclavian artery.

8. The method according to claim 1, wherein inserting the distal end of the first stent graft into the arterial system;
inserting the distal end of the second stent graft into the arterial system;
expanding the first stent graft to fluidicly couple the distal end of the first stent graft to the arterial system;
expanding the second stent graft to fluidicly couple the distal end of the second stent graft to the arterial system;
directing the first portion of the blood from the first egress channel through the first stent graft into the arterial system; and
directing the second portion of the blood from the second egress channel through the second stent graft into the arterial system comprises:
inserting the distal end of the first stent graft into the aorta of a heart;
inserting the distal end of the second stent graft into the left subclavian artery;
expanding the first stent graft to fluidicly couple the distal end of the first stent graft to the aorta of a heart;
expanding the second stent graft to fluidicly couple the distal end of the second stent graft to the left subclavian artery;
directing the first portion of the blood from the first egress channel through the first stent graft into the aorta of a heart; and
directing the second portion of the blood from the second egress channel through the second stent graft into the left subclavian artery.

9. The method according to claim 1, wherein directing the first portion of the blood from the first egress channel through the first stent graft into the arterial system; and directing the second portion of the blood from the second egress channel through the second stent graft into the arterial system comprises:

directing the first portion of the blood from the first egress channel having a first cross-sectional area through the first stent graft into the arterial system; and directing the second portion of the blood from the second egress channel having a second cross-sectional area through the second stent graft into the arterial system, wherein the volume of first and second portions of the blood is determined by relative cross-sectional areas of each of the first and second egress channels.

10. The method according to claim 1, further comprising: reducing the cross-sectional area of at least one of the first or second egress channels using a flow selector.

11. A method of directing blood from a pump to the arterial system using a bifurcated cannula comprising an ingress channel and first and second egress channels, and first and second stent grafts having proximal and distal ends, the method comprising:

fluidicly coupling a first end of a flexible cannula body to the left side of a heart;

fluidicly coupling a second end of the flexible cannula body to the pump;

fluidicly coupling the pump to the ingress channel of the bifurcated cannula;

inserting the distal ends of the first and second stent grafts into the arterial system;

expanding the first stent graft to fluidicly couple the distal end of the first stent graft to the arterial system;

expanding the second stent graft to fluidicly couple the distal end of the second stent graft to the arterial system;

fluidicly coupling the proximal end of the first stent graft to the first egress channel;

fluidicly coupling the proximal end of the second stent graft to the second egress channel;

disengaging the first and second egress channels from the respective proximal ends of the first and second stent grafts; and fluidicly coupling the first and second stent grafts such that the blood flowing in a first direction enters one of the first or second stent grafts and flows into the other of the first or second stent grafts in the first direction and then flows back into the arterial system in the first direction.

12. The method according to claim 11, further comprising:

securing the first and second stent grafts over an outer surface of the respective first and second egress channels of the bifurcated cannula.

* * * * *